(12) United States Patent
Andretta

(10) Patent No.: US 11,529,463 B2
(45) Date of Patent: Dec. 20, 2022

(54) IN-BODY PERFUSION SYSTEM

(71) Applicant: SeralP AG, Stans (CH)

(72) Inventor: Carlo Andretta, Uitikon-Waldegg (CH)

(73) Assignee: SERAIP AG, Stans (CH)

( * ) Notice: Subject to any disclaimer, the term of this patent is extended or adjusted under 35 U.S.C. 154(b) by 420 days.

(21) Appl. No.: 16/609,512

(22) PCT Filed: May 2, 2018

(86) PCT No.: PCT/EP2018/061127
§ 371 (c)(1),
(2) Date: Oct. 30, 2019

(87) PCT Pub. No.: WO2018/202671
PCT Pub. Date: Nov. 8, 2018

(65) Prior Publication Data
US 2020/0069874 A1    Mar. 5, 2020

(30) Foreign Application Priority Data
May 2, 2017    (EP) .................................... 17169158

(51) Int. Cl.
*A61M 5/168* (2006.01)
*A61M 1/36* (2006.01)
*A61M 5/142* (2006.01)

(52) U.S. Cl.
CPC ...... *A61M 5/16813* (2013.01); *A61M 1/3655* (2013.01); *A61M 1/3673* (2014.02); *A61M 5/14276* (2013.01); *A61M 2205/106* (2013.01)

(58) Field of Classification Search
CPC .......... A61M 5/16813; A61M 5/14276; A61M 1/3673; A61M 1/3655; A61M 2205/106; A61F 2/02; A61F 2250/0067
See application file for complete search history.

(56) References Cited

U.S. PATENT DOCUMENTS 5,002,661 A * 3/1991 Chick .................. A61M 1/3472
604/4.01
5,387,237 A * 2/1995 Fournier .................. A61F 2/022
424/424
(Continued)

FOREIGN PATENT DOCUMENTS

CN    101926788 A    12/2010
CN    102240417 A    11/2011
(Continued)

OTHER PUBLICATIONS

World Health Organization (WHO), Global Status Report on non-communicable diseases 2014 (2014).
(Continued)

*Primary Examiner* — Dung T Ulsh
(74) *Attorney, Agent, or Firm* — Agris & von Natzmer, LLP; Joyce von Natzmer

(57) ABSTRACT

An implantable perfusion device (2) comprises a tubular transmission line (4) with an inlet end (6), an outlet end (8) and a flow restriction element (10) located therebetween, whereby an inlet section (12) of the transmission line is defined between the inlet end and the flow restriction element and whereby an outlet section (14) of the transmission line is defined between the flow restriction element and the outlet end. Moreover, the device comprises a perfusion chamber (16) containing a load of biologically active cells and is provided with a fluid entrance (18), a fluid exit (20) and a chamber volume (22) formed therebetween. The fluid entrance comprises at least one first microchannel platelet (24) and the fluid exit comprises at least one second microchannel platelet (26), each one of the microchannel platelets comprising at least one array of microchannels (28) defining a fluid passage between respective external and internal platelet faces, the microchannels having an opening of 0.2 to 10 μm. The fluid entrance (18) of the perfusion chamber is (Continued)

in fluid communication with the inlet section (12) of the transmission line; and the flow restriction element (10) is configured to establish a predetermined pressure excess in the inlet section (12) versus the outlet section (14).

13 Claims, 5 Drawing Sheets

(56) References Cited

U.S. PATENT DOCUMENTS

| | | | |
|---|---|---|---|
| 5,425,764 A * | 6/1995 | Fournier | A61F 2/022 623/23.64 |
| 5,741,334 A * | 4/1998 | Mullon | A61F 2/022 424/424 |
| 6,472,200 B1 | 10/2002 | Mitrani | |
| 2002/0151055 A1 | 10/2002 | Stegemann et al. | |
| 2003/0017142 A1 | 1/2003 | Toner et al. | |
| 2003/0124722 A1 | 7/2003 | Ohgawara et al. | |
| 2010/0166718 A1 | 7/2010 | Matsumoto et al. | |
| 2011/0250585 A1 | 10/2011 | Ingber et al. | |
| 2012/0101590 A1 | 4/2012 | Preuss et al. | |
| 2012/0279881 A1 | 11/2012 | Janko et al. | |
| 2014/0336681 A1* | 11/2014 | Agarwal | A61F 2/00 606/152 |
| 2014/0358060 A1 | 12/2014 | Laster | |
| 2015/0112247 A1* | 4/2015 | Tempelman | A61F 2/022 435/283.1 |
| 2015/0190548 A1 | 7/2015 | Sibbons et al. | |
| 2016/0282164 A1 | 9/2016 | Derevyagin | |
| 2017/0165615 A1 | 6/2017 | Hornung et al. | |

FOREIGN PATENT DOCUMENTS

| | | |
|---|---|---|
| CN | 102317444 A | 1/2012 |
| CN | 102341064 A | 2/2012 |
| CN | 102600521 A | 7/2012 |
| CN | 102614556 A | 8/2012 |
| CN | 103054903 A | 4/2013 |
| CN | 103396986 A | 11/2013 |
| CN | 104379207 A | 2/2015 |
| CN | 104622480 A | 5/2015 |
| CN | 104703634 A | 6/2015 |
| CN | 105056308 A | 11/2015 |
| CN | 204779609 U | 11/2015 |
| CN | 105722582 A | 6/2016 |
| CN | 105917198 A | 8/2016 |
| DE | 4001319 A1 | 7/1991 |
| JP | 2003503022 A | 1/2003 |
| JP | 2003521289 A | 7/2003 |
| JP | 2011528232 A | 11/2011 |
| KR | 101571782 B1 | 11/2015 |
| RU | 2477151 C2 | 3/2013 |
| WO | 9703715 A1 | 2/1997 |
| WO | 0107098 A2 | 2/2001 |
| WO | 02078439 A2 | 10/2002 |
| WO | 2004110256 A2 | 12/2004 |
| WO | 2008114218 A2 | 9/2008 |
| WO | 2014109898 A1 | 7/2014 |

OTHER PUBLICATIONS

Li, Yan et al., Subcutaneous implantation system and treatment of type 2 diabetes mellitus, Journal of Chinese Academy of Medical Sciences, 33(4):473-477 (2011) (English abstract).

* cited by examiner

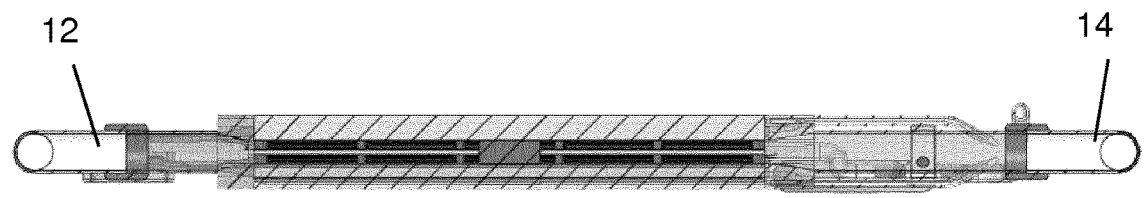
Fig. 11
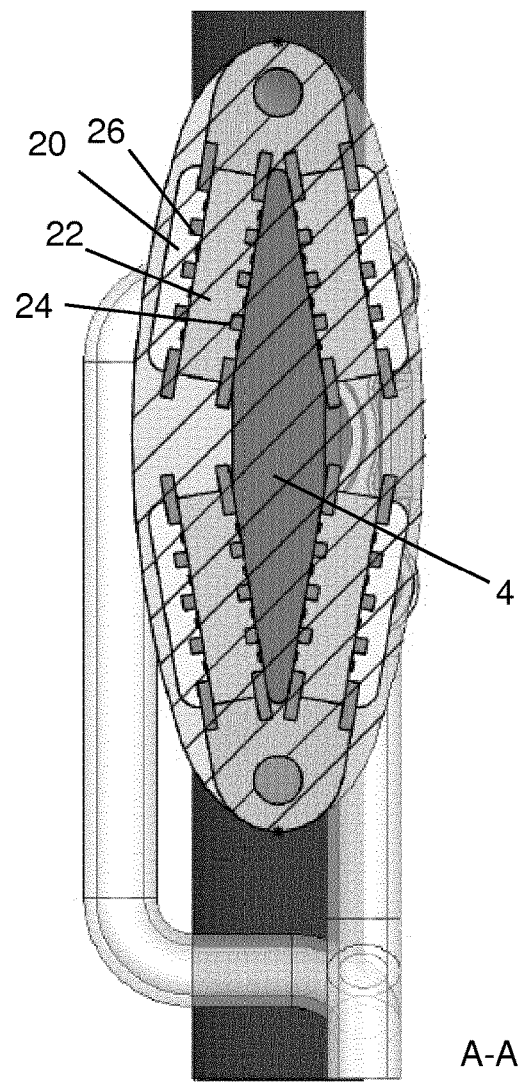
Fig. 12  A-A
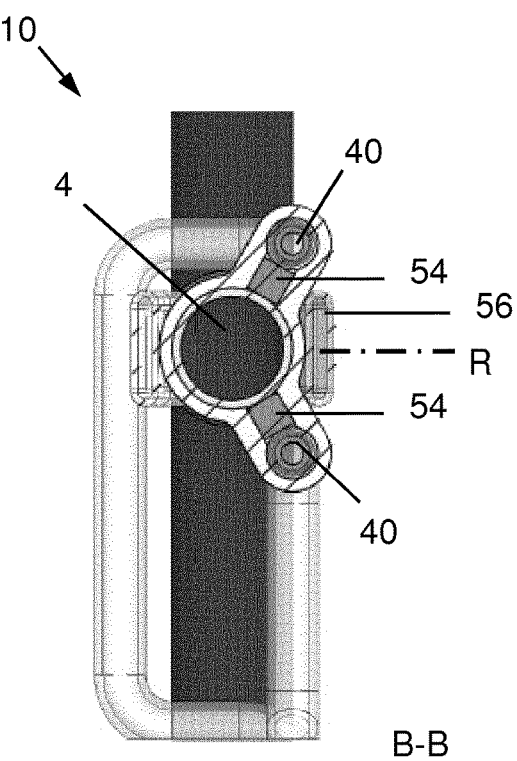
Fig. 13  B-B
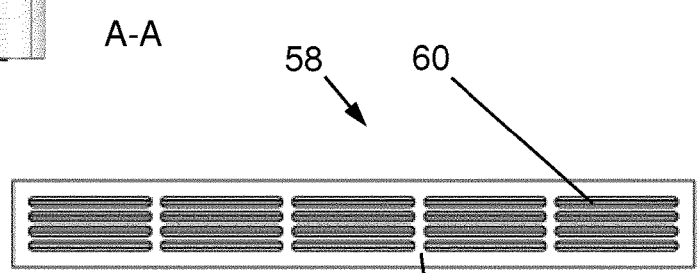
Fig. 14

IN-BODY PERFUSION SYSTEM

CROSS-REFERENCE TO RELATED APPLICATIONS

This is the U.S. national stage of International application PCT/EP2018/061127, filed May 2, 2018 designating the United States and claiming priority to European Patent application EP 17169158.7, filed May 2, 2017.

FIELD OF THE INVENTION

The present invention generally relates to an in-body perfusion system. More specifically, the invention relates to an implantable perfusion device containing a load of biologically active cells.

BACKGROUND OF THE INVENTION

According to the World Health Organization, in 2014 the global prevalence of diabetes was estimated to be 9% among adults aged 18 or more (Global status report on noncommunicable diseases 2014. Geneva, World Health Organization, 2012). Treatment of diabetes involves lowering blood glucose and the levels of other known risk factors that damage blood vessels. For patients with type 1 diabetes, but also for patients with progressed forms of type 2 diabetes, the necessary interventions include administration of insulin. Because of inevitable variations in external influencing factors and often also because of a lack of discipline, the glucose levels in blood often fluctuate substantially, which can lead to a number of complications of the vascular and nervous systems. For such patients, insulin pumps have gained increasing popularity. Most of these pumps emit insulin continuously at a low-dosage basal rate which can be increased on demand, notably before meals. In order to optimize use of an insulin pump, it is highly desirable to also have a system for continuous or periodic monitoring of the blood glucose level.

The combination of an insulin pump and an appropriate control system which relies on a feedback signal from a blood glucose monitoring system can be considered as a "medical technology" variant of an artificial pancreas. Such a glucose measuring module and insulin pump combination has been disclosed e.g. in WO 2004/110256 A2. Optimum control of such devices represents a challenge, as may be appreciated e.g. from WO 2014/109898 A1, which describes a model-based personalization scheme of an artificial pancreas for type I diabetes applications.

An alternative type of artificial pancreas that is structurally more similar to a real pancreas is based on an implanted bioengineered tissue containing islet cells which deliver endocrine insulin in response to glucose. One concept of such a bio-artificial pancreas utilizes encapsulated islet cells forming an islet sheet which is suitable for surgical implantation in a patient. The islet sheet typically comprises the following components: (1) an inner mesh of supporting fibers forming a sheet-like structure, (2) a plurality of islet cells which are encapsulated in order to avoid triggering of an immune reaction and which are adhered to the mesh fibers, (3) a semi-permeable protective layer around the sheet which allows diffusion of nutrients and of hormones secreted by the islet cells, and (4) a protective outer coating to prevent a foreign body response.

US 2002/0151055 A1 discloses a bio-artificial pancreas which comprises viable and physiologically active pancreatic islet cells capable of producing insulin encapsulated within a semipermeable spheroidal membrane comprising agar gel. The artificial pancreas can be installed within a diffusion chamber or a perfusion chamber containing hollow fibers. Exemplary perfusion devices consist of a membrane inside an acrylic housing with blood flowing axially through the membrane and insulin being secreted by islets radially through the membrane into the blood. Such a perfusion-based bio-artificial pancreas has been disclosed in U.S. Pat. No. 5,741,334.

A notorious difficulty encountered when operating a bio-artificial pancreas of the above described type is related to the requirement of a sufficiently large and durable substance transport rate to and from the encapsulated islet cells. On the one hand it is necessary to ensure a sufficient supply rate of nutrients to the islet cells and, of course, for a corresponding removal rate of the insulin produced by the islet cells. On the other hand, the components of the bio-artificial pancreas need to have a constant performance over an extended period of time. In particular, any clogging or collapsing of the semi-permeable protective layer shall be avoided.

SUMMARY OF THE INVENTION

It is thus an object of the present invention to provide an improved system suitable for operation as bio-artificial pancreas that does not suffer from the above-mentioned disadvantages.

According to one aspect of the invention, there is provided an implantable perfusion device, comprising:
  a tubular transmission line with an inlet end, an outlet end and a flow restriction element located therebetween, whereby an inlet section of the transmission line is defined between the inlet end and the flow restriction element and whereby an outlet section of the transmission line is defined between the flow restriction element and the outlet end,
  a perfusion chamber comprising a fluid entrance, a fluid exit and a chamber volume formed therebetween;
  the perfusion chamber containing a load of biologically active cells: the fluid entrance comprising at least one first microchannel platelet and the fluid exit comprising at least one second microchannel platelet, each one of the microchannel platelets comprising at least one array of microchannels defining a fluid passage between respective external and internal platelet faces, the microchannels having an opening of 0.2 to 10 µm;
  each one of the microchannel platelets being sealingly connected to a circumferentially surrounding wall section of the perfusion chamber; wherein
  the fluid entrance of the perfusion chamber is in fluid communication with the inlet section of the transmission line;
and wherein
  the flow restriction element is configured to establish a predetermined pressure excess in the inlet section versus the outlet section.

In the present context, the singular form used to denote certain features shall be understood to include the possibility of having multiple features achieving a technically equivalent effect. In particular, the term "perfusion chamber" shall also apply to embodiments in which multiple chambers effectively cooperate as a single functional unit.

The perfusion chamber is configured to contain biologically active cells in a confined environment while ensuring sufficient substance transport into and out of the chamber. For this purpose, the microchannel platelets forming the fluid entrance and the fluid exit of the perfusion chamber provide an appropriate filtering function. Accordingly, the optimum size of the microchannels will depend on the particular application. In general, it will be selected in the range of 0.2 to 10 µm. The lower limit is primarily determined by the available forming technology, but also by the need to have sufficient throughput. The upper limit is determined by the size of particles that should be prevented from passing through the microchannels. For many applications the microchannels should have an opening in the range of 0.9 to 2.2 µm, most typically of around 1.6 µm. The term "opening" shall be understood as the diameter in the case of microchannels with circular cross section; for non-circular microchannels the term "opening" shall be understood as the smallest transversal size of the cross section. Currently available technologies for forming openings with the above-mentioned diameter range usually require a height to diameter ratio ("aspect ratio") of up to 5. In other words, the thickness of a microchannel platelet in the region surrounding the microchannels needs to be small enough, i.e. in the range of 1 to 50 µm depending on the microchannel diameter. In order to provide sufficient stiffness of the front platelet, reinforcing regions with a substantially higher thickness are provided at locations displaced from the microchannels.

In order to meet the basic requirements of cell containment, each one of the microchannel platelets of the device is sealingly connected to a circumferentially surrounding wall section of the perfusion chamber. The term "circumferentially" does not imply a circular shape and is merely intended to define a closed loop as needed to form an uninterrupted seal along a platelet edge.

The perfusion device is intended for implantation in a human or mammal in such manner that the tubular transmission line forms a so-called arterio-venous (AV) shunt connecting an artery and a vein. For example, the device can be implanted in the forearm of a human patient. A substantial pressure difference between the arterial and the venous system induces a pressure gradient along the transmission line. This pressure gradient tends to drive arterial blood into the transmission line at its inlet end and out of the transmission line at its outlet end. The presence of a perfusion chamber in fluid communication with the tubular transmission line effectively forms a bifurcation for the blood. Therefore, as explained in more detail further below, a fraction of the blood flow occurs through the perfusion chamber, i.e. blood flows into the perfusion chamber through its fluid entrance and leaves the perfusion chamber through its fluid exit. After leaving the perfusion chamber, the blood is either reconducted into the tubular transmission line or it is allowed to flow into other body regions. For convenience, the flow path directly leading through the transmission line will henceforth be called "AV flow" whereas the blood flow occurring through the perfusion chamber will be called "perfusion flow". In accordance with the flow dynamics of substantially incompressible fluids, the branching ratio between perfusion flow and AV flow is determined by the ratio of flow conductances of the two pathways.

The flow conductance of the tubular transmission line, which has a typical opening of the order of a few millimeters, i.e. somewhere in the range of about 2 to about 10 mm, particularly about 3 to 8 mm, in the absence of any substantial flow restrictions is larger than the flow conductance through the perfusion chamber, which passes through a pair of microchannel platelets forming the fluid entrance and the fluid exit of the perfusion chamber. Therefore, in order to establish a sufficient perfusion flow, it is necessary to reduce the AV flow by providing an appropriately dimensioned flow restriction element. In practice, the flow restriction element can achieve a pressure buildup of about 100 mbar in the inlet section of the transmission line.

The implantable perfusion device of the present invention is generally intended to contain biologically active cells which produce one or more useful substances, henceforth also called "cell product", to be supplied to the hosting organism in need thereof. To fulfil this purpose, the perfusion cell should have a sufficiently large volume in order to contain an appropriately large number of cells. Moreover, the perfusion flow serving to ensure an adequate supply rate of nutrients and an appropriate removal rate of the cell product needs to be sufficiently large. In a typical configuration, the perfusion chamber can have a chamber volume of several ml, e.g. about 5 to 6 ml and contain about 50 million cells per ml. By having a flat and elongated size with a length of up to about 10 cm, the perfusion chamber can have a total area of the microchannels of several 100 $mm^2$.

As used herein, the term "biologically active cells" shall be understood in a broad context. In particular, such biologically active cells may be obtained as classically differentiated cells starting from human stem cells and applying a suitable genetic or non-genetic differentiation mechanism. Alternatively, they may be provided as transplanted cells, i.e. as xenotransplanted cells including, as the case may be, bacteria, or as autologously or allogeneically transplanted human cells.

Advantageous embodiments are defined in the dependent claims and are described below.

According to one embodiment (claim 2), the fluid exit of the perfusion device is in fluid communication with the outlet section of the transmission line. In other words, the perfusion flow is guided back into the AV flow at a location down-stream of the flow restriction element. This means that the cell product is delivered into the venous bloodstream.

It is contemplated that the cell product may be delivered to a particular region or organ, in which case the perfusion flow would have to be guided by appropriate means.

In a further embodiment (claim 3), the fluid exit of the perfusion device is configured for fluid delivery to an interstitial body region. Accordingly, the device is implanted in such manner that the microchannel platelet forming the fluid exit is in direct contact with surrounding tissue. This embodiment is considered useful, for example, for use in test animals.

Advantageously (claim 4), the device further comprises means for controlling a restriction characteristic of the flow restriction element. In particular, this may comprise a flow restriction element having a movable member controlled by an appropriate steering unit. In this manner, it is possible to implement controlled variations of the flow restriction with concomitant changes in the ratio of perfusion and AV flow. In one embodiment, the flow restriction is operated in an oscillatory manner, which could be an on-off scheme with fully open and fully closed positions. It is contemplated that the on-off scheme may have a duty cycle, i.e. a ratio of "on" to "off" time different from 1. An important advantage of having a controllable flow restriction is related to undesirable side effects caused by an uninterrupted and unhindered blood flow from the artery to the vein, which may result e.g. in numbness of the hand.

According to one embodiment (claim 5), the controlling means comprise a driven reciprocating plug member cooperating with an appropriately formed counterpart acting as a seat. For example, the plug member may be a bar magnet that can move bidirectionally in a channel-like counterpart and is driven by an external magnet performing a cyclic motion.

In many applications it is advantageous or even necessary to provide some kind of anticoagulation agent such as heparin or citrate. Therefore, according to yet another embodiment (claim 6), the device further comprises means for supplying a liquid agent to the chamber volume. Such means may comprise a suitable container, which may be configured as a subcutaneous injection port, a supply line connecting the container and the perfusion chamber, and an appropriate pumping device. In some embodiments, internal surfaces of the implantable perfusion device are provided with an anticoagulation coating, e.g. a heparin coating.

According to a particularly advantageous embodiment (claim 7) the supplying means comprise a pair of unidirectional valves cooperating with the reciprocating plug member acting on a fluid line segment connecting the valve pair. In other words, the reciprocating plug member driven, e.g. by an external magnet, is used both to produce an intermittent modulation of perfusion flow and to pump a liquid agent such as citrate through the perfusion chamber.

In certain cases, particular when used on test animals for a comparatively short period of days or up to a few weeks, perfusion device can be operated with an initial load of active cells. In most applications, however, it will be necessary to supply fresh active cells. Therefore, according to an advantageous embodiment (claim 8) the perfusion device further comprises means for loading and unloading a cell population into the chamber volume. These can be implemented as a subcutaneously implantable injection port equipped with tubing forming a connection to the perfusion chamber and furthermore provided with appropriate valves.

An important factor for achieving an efficient operation of the perfusion device is having a sufficiently large total area of the microchannels. However, production of very large microchannel plates is impractical in view of inevitable production failures leading to occasional oversized channels. Evidently, a single oversized channel results in a loss of cell containment and thus is not acceptable. Therefore, according to an advantageous embodiment (claim 9), the fluid entrance and/or the fluid exits comprise a plurality of microchannel platelets. With such a modular design utilizing several small platelets instead of a single large platelet, the failure of a single channel merely requires discarding a comparatively small unit of the entire surface.

Advantageously, the microchannel platelets are made of material that is suitable to a photolithographic processing, which is a very convenient technique for forming narrow structures with a well-defined shape. Therefore, according to an advantageous embodiment (claim 10), the microchannel platelets are made of silicon (Si) and/or silicon nitride ($Si_3N_4$). Moreover, at least the circumferentially surrounding wall section of the perfusion chamber is made of a material that is compatible with that of the front platelet and that has advantageous properties in view of any fluid connections to be attached thereto. Suitable sandwich structures made of Si and $Si_3N_4$ layers are generally known in the field of microtechnology. In some embodiments the microchannel platelet is functionalized, i.e. provided with a suitable coating. The type and thickness of such coating will depend on the particular application. For the contact with blood there are known functionalizations aiming at the prevention of clot formation and coagulation.

According to an advantageous embodiment (claim 11), the microchannel platelets and the circumferentially surrounding wall section are joined to each other by anodic bonding. In particular, this method allows formation of strong and medium-tight connections between Si and glass structures. Alternatively, the connection can be formed by means of an adhesive.

Suitable locations and configurations for the implantable perfusion device are straight forearm (radial artery to cephalic vein), looped forearm (brachial artery to cephalic vein) and straight upper arm (brachial artery to basilica or axillary vein). Further possibilities are thigh grafts, necklace grafts (axillary artery to axillary vein), and axillary-atrial grafts. Therefore, according to an advantageous embodiment the tubular transmission line is provided at its inlet end and outlet end with means for connecting to a patient's artery and vein, respectively (claim 12). Preferably, these are releasable connecting means. This embodiment will allow connecting the device's tubular line, which is typically made of a biocompatible thermoplastic with advantageous formability properties, onto a counterpart consisting of the synthetic graft tubing connected to the patient's artery or vein. Such graft tubings are typically made of polytetrafluoroethylene (PTFE).

As already mentioned, the perfusion device is suitable for use with a load of biologically active cells, which cells can be selected according to a particular task to be achieved. According to one embodiment, the biologically active cells loaded in the perfusion chamber are islet of Langerhans cells (LC). As will be understood, the cell product will in this case be insulin, and the perfusion device can thus be implemented as forming part of an artificial pancreas device.

BRIEF DESCRIPTION OF THE DRAWINGS

The above mentioned and other features and objects of this invention and the manner of achieving them will become more apparent and this invention itself will be better understood by reference to the following description of various embodiments of this invention taken in conjunction with the accompanying drawings, wherein:

FIG. 11 shows the part of FIG. 10, in a longitudinal sectional view;

FIG. 12 shows the part of FIG. 10, in a cross-sectional view according to section A-A of FIG. 10;

FIG. 13 shows the part of FIG. 10, in a cross-sectional view according to section B-B of FIG. 10; and FIG. 14 shows an arrangement of 5 times 4 microchannel platelets, in a top view.

DETAILED DESCRIPTION OF THE INVENTION

It will be understood that the figures are not necessarily drawn to scale. In some instances, relative dimensions are substantially distorted for ease of visualization.

Figure 1:
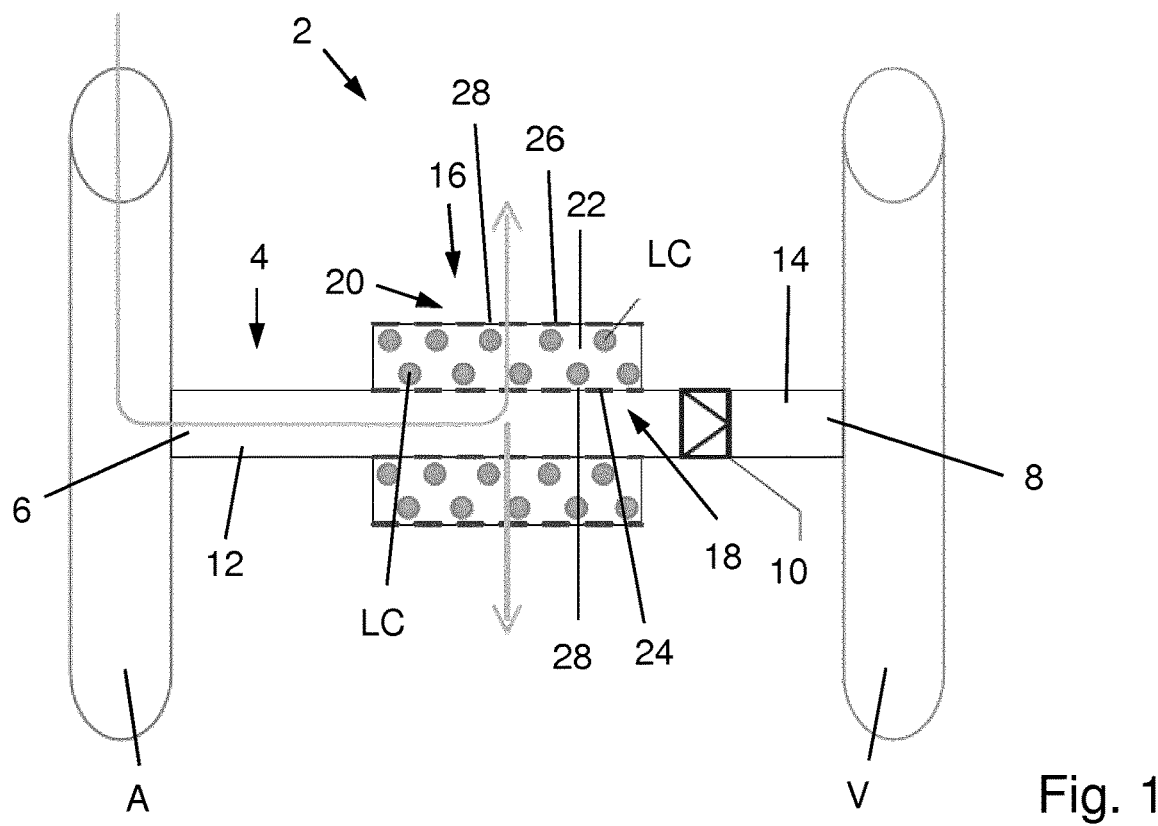
FIG. 1 shows a first embodiment of a fluid interface device, in a sectional view.

The perfusion device 2 shown in FIG. 1, which is implanted as a shunt between an artery A and a vein V, comprises a tubular transmission line 4 with an inlet end 6, an outlet end 8 and a flow restriction element 10 located therebetween. As seen from FIG. 1, the flow restriction element 10 defines, on the left side, an inlet section 12 located between the inlet end 6 and the flow restriction element, and it further defines an outlet section 14 located between the flow restriction element and the outlet end 8. The flow restriction element 10 serves to establish a predetermined pressure excess in the inlet section 12 versus the outlet section 14.

The device furthermore has a perfusion chamber 16 comprising a fluid entrance 18, a fluid exit 20 and a chamber volume 22 formed therebetween. In the example shown, the perfusion chamber actually comprises an upper part and a completely equivalent lower part, which for simplicity is not provided with reference numerals and is not discussed further here.

The fluid entrance comprises a first microchannel platelet 24, and the fluid exit comprises a second microchannel platelet 26, each one of these platelets comprising an array of microchannels 28 defining a fluid passage between respective external and internal platelet faces. As also seen from FIG. 1, the fluid entrance 18 of the perfusion chamber is in fluid communication with the inlet section 12 of the transmission line;

In the example shown in FIG. 1, the fluid exit 20 of the perfusion device is configured for fluid delivery of the cell product formed in the chamber volume 22 to an interstitial tissue located between the artery A and the vein V.

Figure 2:
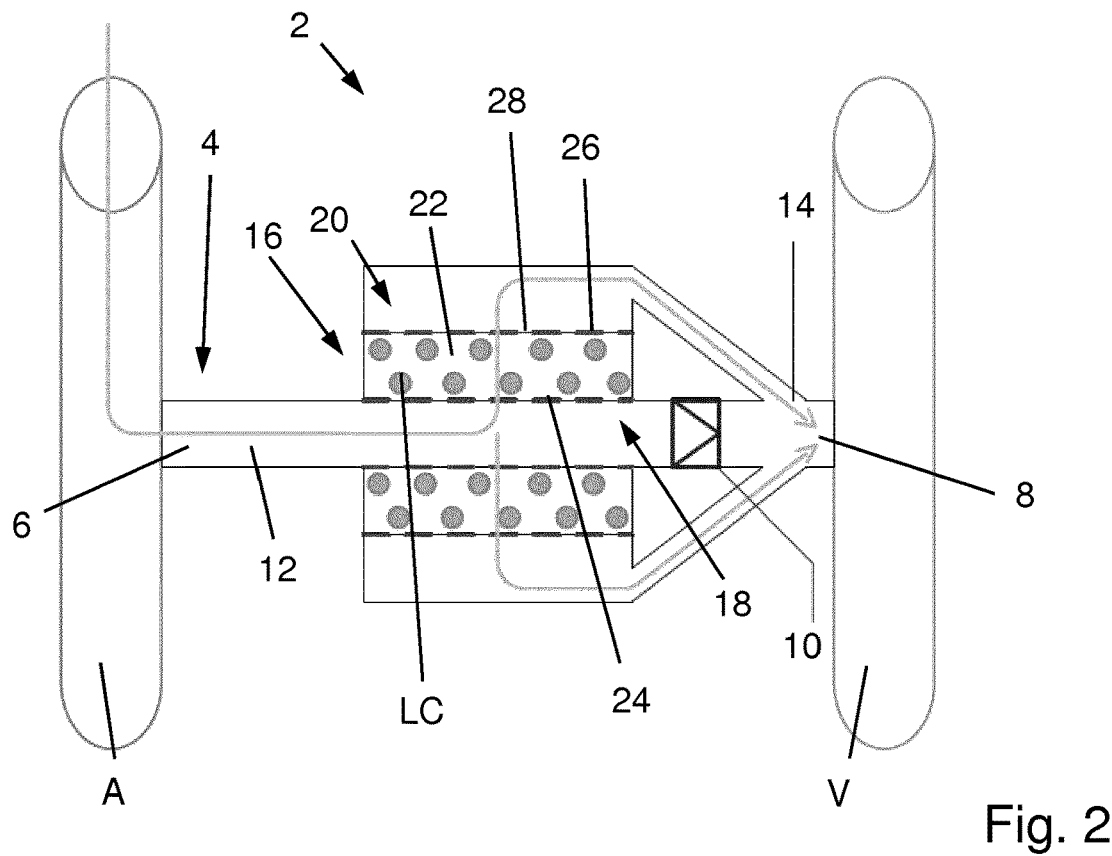
FIG. 2 shows a second embodiment of a fluid interface device, in a sectional view.

The perfusion device 2 shown in FIG. 2 has many of the features already discussed in relation to FIG. 1 and which need no further discussion. In contrast to the embodiment of FIG. 1, however, the fluid exit 20 of the perfusion device leads into the outlet section 14 of the transmission line. Accordingly, cell product formed in the chamber volume 22 is led through the outlet section 14 and into the venous bloodstream.

Figure 3:
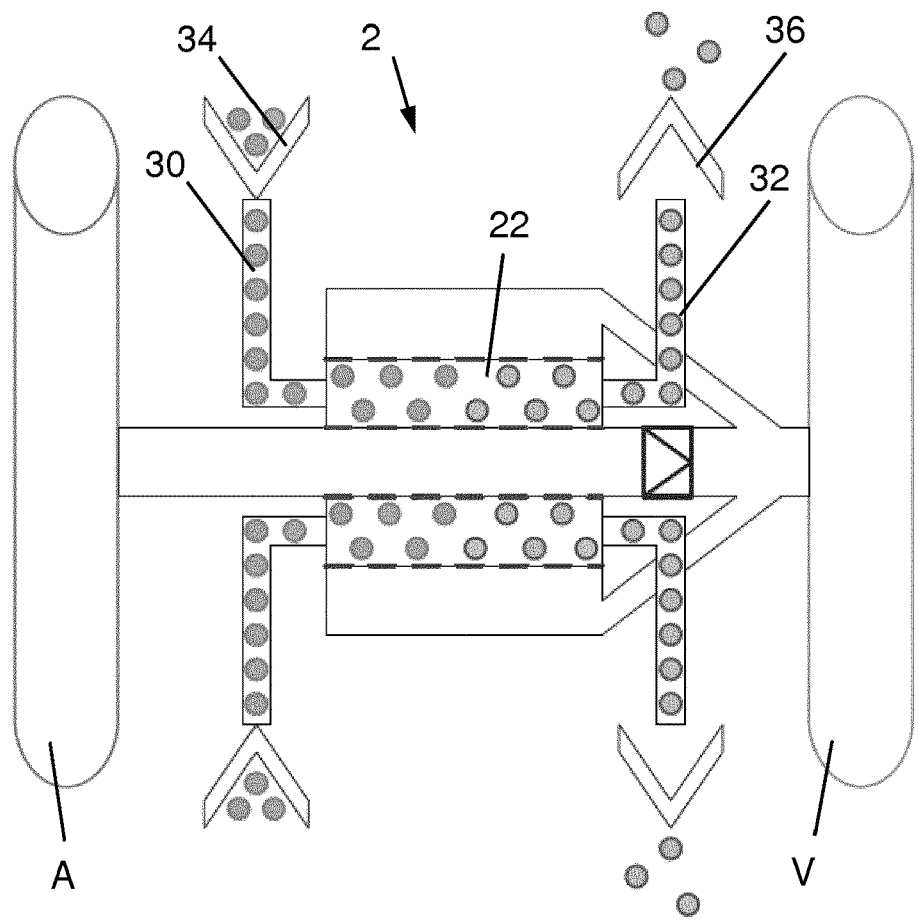
FIG. 3 shows a third embodiment of a fluid interface device, in a sectional view.

The perfusion device 2 shown in FIG. 3 corresponds to the embodiment shown in FIG. 2 and further comprises means for loading and unloading a cell population into the chamber volume 22. These means comprise a loading line 30 and an unloading line 32, each provided with appropriate valves schematically shown as 34 and 36, respectively.

The perfusion device 2 shown in FIG. 4 again corresponds to the embodiment shown in FIG. 2 and further comprises means for supplying a liquid agent such as a citrate solution to the chamber volume 22. These means comprise a container 38, a supply line 40 connecting the container 38 and the perfusion chamber 22, and an appropriate pumping device 42.

Figure 4:
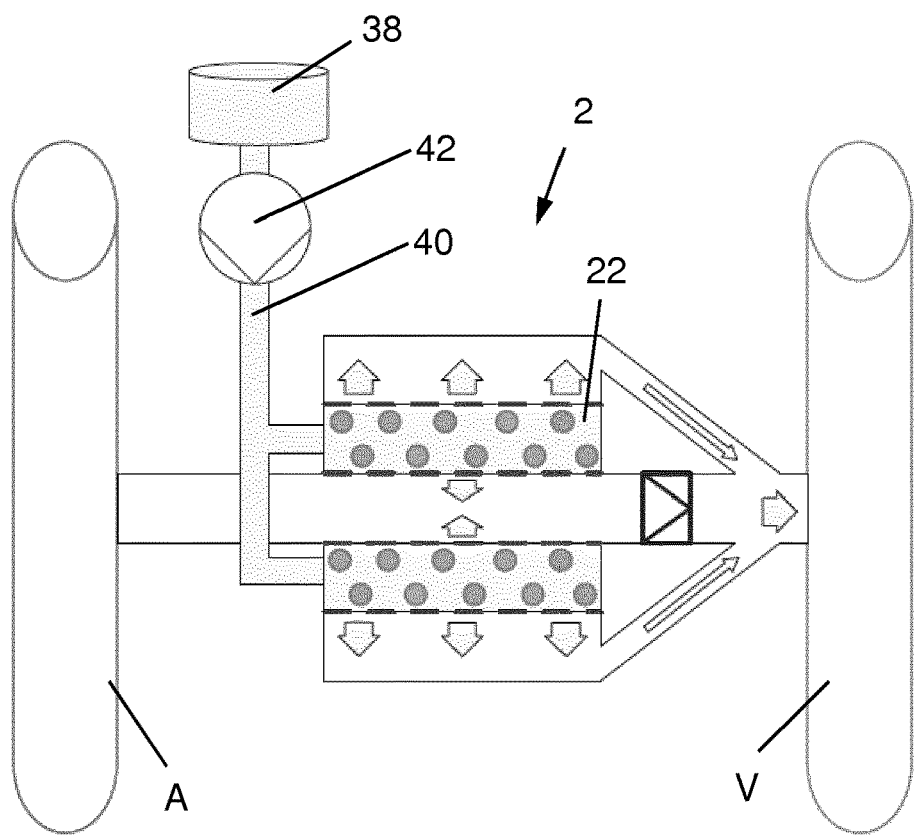
FIG. 4 shows a fourth embodiment of a fluid interface device, in a sectional view.
Figure 5:
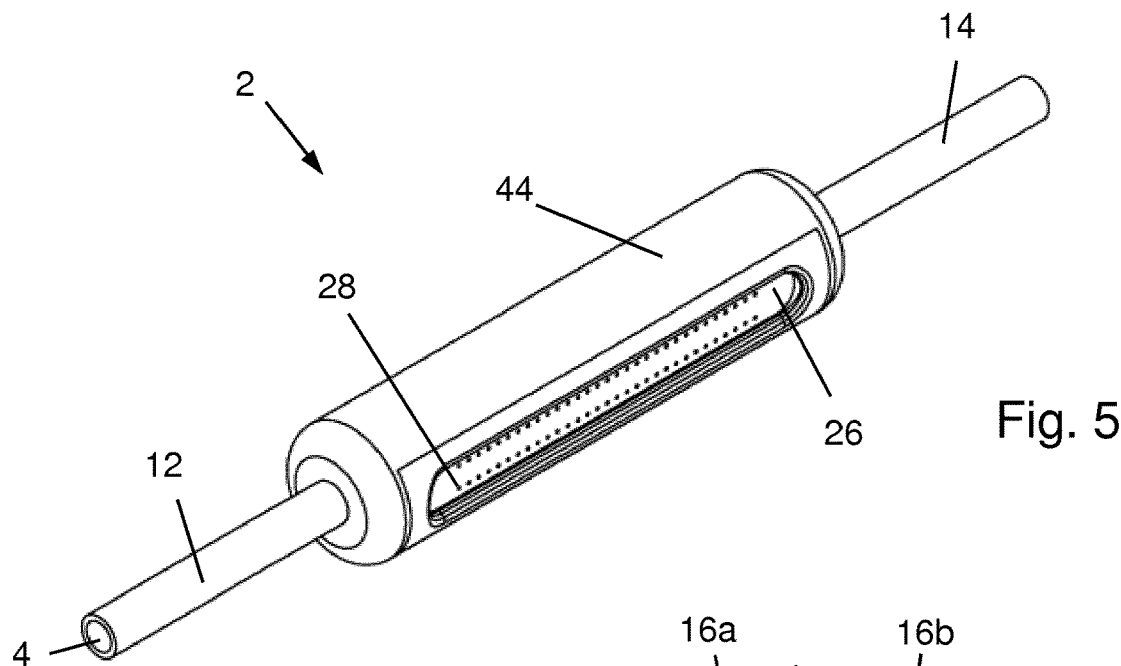
FIG. 5 shows a central part of the first embodiment, in a perspective view.
Figure 7:
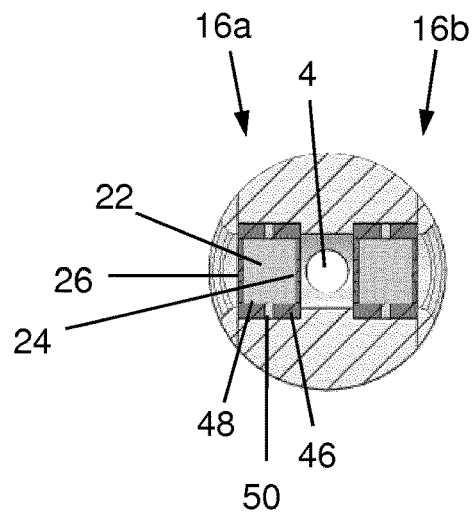
FIG. 7 shows the part of FIG. 6, in a cross-sectional view.
Figure 6:
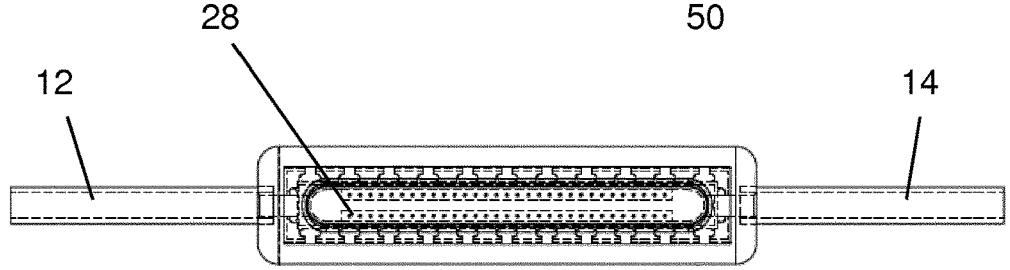
FIG. 6 shows the part of FIG. 6, in a top view.
Figure 8:
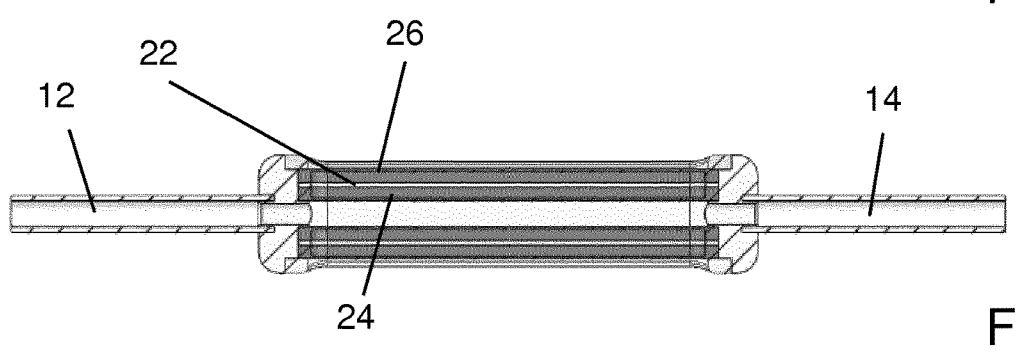
FIG. 8 shows the part of FIG. 6, in a longitudinal sectional view.
Figure 9:
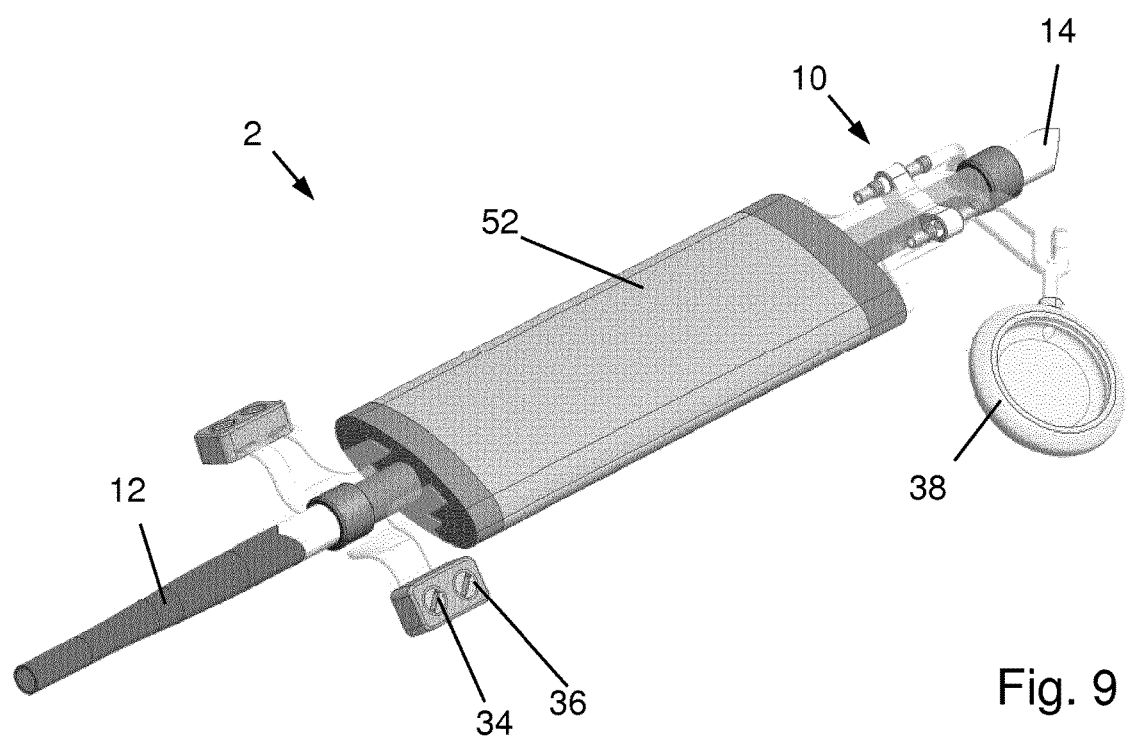
FIG. 9 shows a central part of a fifth embodiment, in a perspective view.
Figure 10:
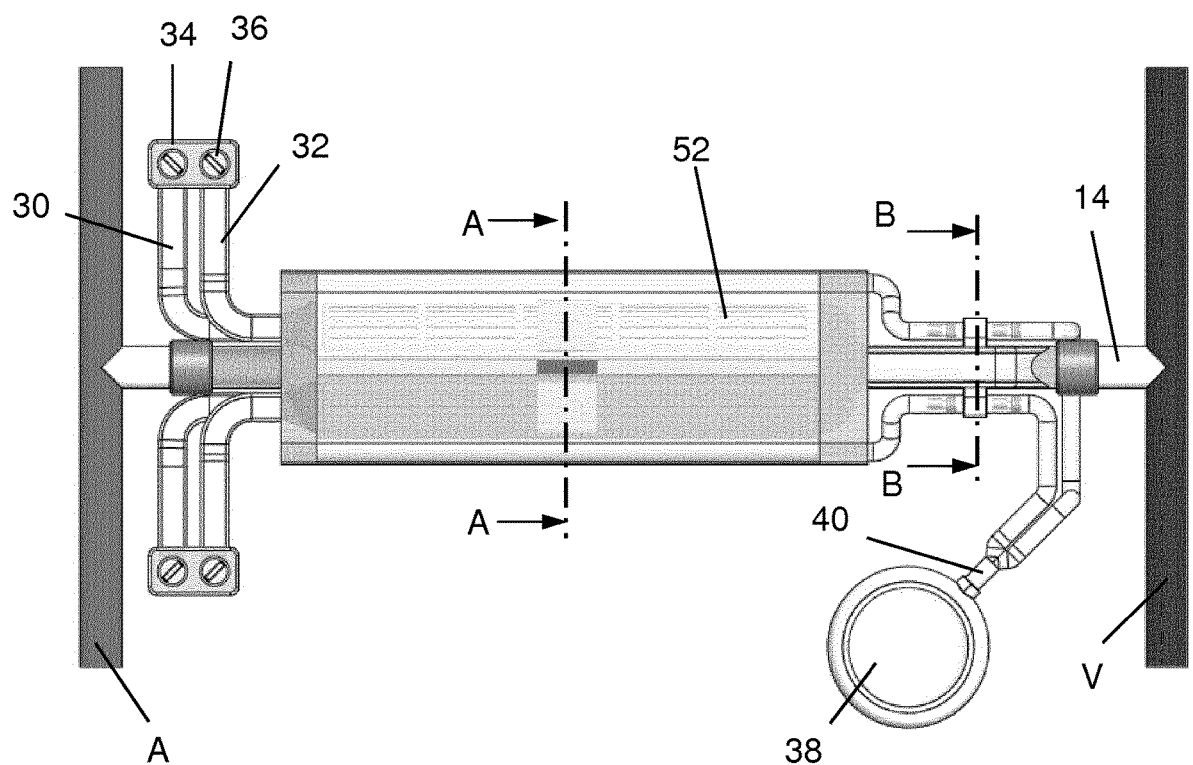
FIG. 10 shows the part of FIG. 9, in a top view.

In practice, both embodiments of FIGS. 3 and 4 are usually implemented together and are shown here separately merely for ease of drawing.

An embodiment intended for delivery to interstitial tissue is shown in more detail in FIGS. 5 to 8, whereas an embodiment intended for delivery to the venous bloodstream is shown in more detail in FIGS. 9 to 14. Any features that have already been explained above will generally not be discussed again; in some instances, they are merely indicated by the respective reference numeral.

The device 2 shown in FIGS. 5 to 8 features an elongated, substantially circularly cylindrical housing 44 forming a central part of a tubular transmission line 4 having an inlet section 12 and outlet section 14. The housing 44 accommodates two perfusion chambers 16a and 16b located at opposite sides of the transmission line 4 in a symmetric manner. Each perfusion chamber comprises a first microchannel platelet 24 adjacent to the transmission line and a second microchannel 26 substantially parallel to the first microchannel platelet and displaced radially away therefrom. Thereby, a chamber volume 22 is formed between the two platelets. As also shown notably in FIG. 7, each microchannel platelet is sealingly connected to a wall section of the housing. In particular, a first wall section 46 connected to the first microchannel platelet 24 and a second wall section 48 connected to the second microchannel platelet 26 are joined together in a sandwich manner at a contact region 50.

The device 2 shown in FIGS. 9 to 12 comprises an elongated, substantially elliptically cylindrical housing 52. The entire device is configured in a relatively flat shape which allows construction of comparatively long microchannel regions providing a large fluid exchange surface with a concomitantly large perfusion flow. The device has a cell loading line 30 and a cell unloading line 32 which are flat shaped and each provided with appropriate valves 34 and 36, respectively.

FIG. 12 shows the flow paths of the device which is configured in a three-compartment manner. Arterial blood supplied via the tubular transmission line 4 is located in an innermost, primary compartment, from which blood can flow through a first microchannel platelet 24 into the perfusion chamber 22, which forms a secondary compartment containing an active cell population. From there, blood containing cell product flows through a second microchannel platelet 24 into the exit section 20 forming a tertiary compartment which is in communication with the outlet section 14 of the device.

FIG. 13 illustrates an operating principle of a controllable flow restriction element 10. The latter comprises a pair of reciprocating plug members 54 each containing a permanent magnet. Each plug member can reciprocate between a retracted position (as shown in the figure) and an inserted position (not shown) in which the plug pushes inwards and compresses a tube segment of the tubular transmission line 4. The reciprocating motion is induced by a disk shaped external magnet 56 that rotates about an axis R. In the example shown, the plug members 54 furthermore act as squeezing members for a flexible segment of the anticoagulant supply line 40 located between a pair of unidirectional valves (not shown) having a common throughput direction.

As seen from FIG. 14, a chamber wall 58 acting as fluid entrance or fluid exit is formed by a plurality of microchannel platelets 60 arranged as a matrix of 4×5 elements in the example shown. Each platelet is sealing connected to a circumferentially surrounding wall section 62 of the chamber wall.

The invention claimed is:

1. An implantable perfusion device, comprising:
   a tubular transmission line with
      an inlet end,
      an outlet end and
      a flow restriction element located therebetween,
   wherein an inlet section of the transmission line is defined
      between the inlet end and the flow restriction element
      and
   wherein an outlet section of the transmission line is
      defined between the flow restriction element and the
      outlet end,
   a perfusion chamber comprising:
      a fluid entrance,
      a fluid exit and a chamber volume formed therebetween;
the perfusion chamber containing a load of biologically active cells;
the fluid entrance comprising
at least one first microchannel platelet and
the fluid exit comprising
at least one second microchannel platelet,
each one of the microchannel platelets comprising at least one array of microchannels defining a fluid passage between respective external and internal platelet faces, the microchannels having an opening of 0.2 to 10 μm;
each one of the microchannel platelets being sealingly connected to a circumferentially surrounding wall section of the perfusion chamber;
wherein
the fluid entrance of the perfusion chamber is in fluid communication with the inlet section of the transmission line;
and wherein
the flow restriction element is configured to establish a predetermined pressure excess in the inlet section versus the outlet section.

2. The perfusion device according to claim 1, wherein the fluid exit of the perfusion chamber is in fluid communication with the outlet section of the transmission line.

3. The perfusion device according to claim 1, wherein the fluid exit of the perfusion chamber is configured for fluid delivery to an interstitial body region.

4. The perfusion device according to claim 1, further comprising a controlling element configured to control a restriction characteristic of the flow restriction element.

5. The perfusion device according to claim 4, wherein the controlling element comprises a driven reciprocating plug member.

6. The perfusion device according to claim 5, further comprising a supplying element configured to supply a liquid agent to the chamber volume, wherein said supplying element comprises a pair of unidirectional valves cooperating with the reciprocating plug member acting on a fluid line segment connecting the pair of valves.

7. The perfusion device according to claim 1, further comprising a supplying element configured to supply a liquid agent to the chamber volume.

8. The perfusion device according to claim 1, further comprising elements configured to load and unload a cell population into the chamber volume.

9. The perfusion device according to claim 1, wherein the fluid entrance and/or the fluid exits comprise(s) a plurality of the microchannel platelets.

10. The perfusion device according to claim 1, wherein the first and/or second micro-channel platelets are made of Si and/or $Si_3N_4$.

11. The perfusion device according to claim 1, wherein the first micro-channel platelets are sealingly connected to a circumferentially surrounding wall section of the perfusion chamber by anodic bonding.

12. The perfusion device according to claim 1, wherein the tubular transmission line is provided at its inlet end and outlet end with a connector configured to connect to a patient's artery and vein, respectively.

13. The perfusion device according to claim 1, wherein the biologically active cells loaded in the perfusion chamber are islet of Langerhans cells (LC).

* * * * *